US008038695B2

(12) United States Patent
Kim

(10) Patent No.: US 8,038,695 B2
(45) Date of Patent: Oct. 18, 2011

(54) CONSECUTIVE ACUPUNCTURE DEVICE

(75) Inventor: Hyeon Ho Kim, Gwangjin-gu (KR)

(73) Assignee: Neo DR. Inc. (KR)

( * ) Notice: Subject to any disclaimer, the term of this patent is extended or adjusted under 35 U.S.C. 154(b) by 156 days.

(21) Appl. No.: 11/718,818

(22) PCT Filed: Feb. 14, 2006

(86) PCT No.: PCT/KR2006/000520
§ 371 (c)(1), (2), (4) Date: May 8, 2007

(87) PCT Pub. No.: WO2006/095966
PCT Pub. Date: Sep. 14, 2006

(65) Prior Publication Data
US 2008/0097505 A1 Apr. 24, 2008

(51) Int. Cl.
*A61B 17/34* (2006.01)

(52) U.S. Cl. ......................... 606/189; 606/182; 606/186

(58) Field of Classification Search .................. 606/189, 606/186, 181, 182
See application file for complete search history.

(56) References Cited

U.S. PATENT DOCUMENTS 4,580,566 A * 4/1986 Hsu ............................... 606/189
5,954,738 A * 9/1999 LeVaughn et al. ............ 606/181
6,113,620 A * 9/2000 Chung .......................... 606/189
2004/0167548 A1* 8/2004 Bonutti ......................... 606/144
2005/0067310 A1* 3/2005 Choi ............................. 206/366
2005/0277973 A1* 12/2005 Huang et al. .................. 606/185
2006/0155210 A1* 7/2006 Beckman et al. ............. 600/567
2006/0247671 A1* 11/2006 LeVaughn ..................... 606/182
2008/0228212 A1* 9/2008 List .............................. 606/182

FOREIGN PATENT DOCUMENTS

WO WO 2004/009010 * 1/2004

* cited by examiner

*Primary Examiner* — Anhtuan Nguyen
*Assistant Examiner* — Julie A Szpira
(74) *Attorney, Agent, or Firm* — Hershkovitz & Associates, LLC; Abraham Hershkovitz

(57) ABSTRACT

A consecutive acupuncture device for consecutively inserting needles into afflicted sites of the body. The device comprises a cartridge charged with and storing one or more needles, a first magnet positioned at a side of the cartridge to pull a needle stored in the cartridge by magnetic force and automatically place the needle at a striking position, striking means positioned on the cartridge to strike the needle placed at the striking position and insert the needle into an afflicted site of the body, and a discharge section positioned underneath the cartridge and defined with a hole through which the needle struck by the striking means is discharged. By storing one or more needles in the cartridge in a disarranged state and pressing a button, the stored needles can be driven one by one into the afflicted sites of the body.

6 Claims, 9 Drawing Sheets

【Figure 1】
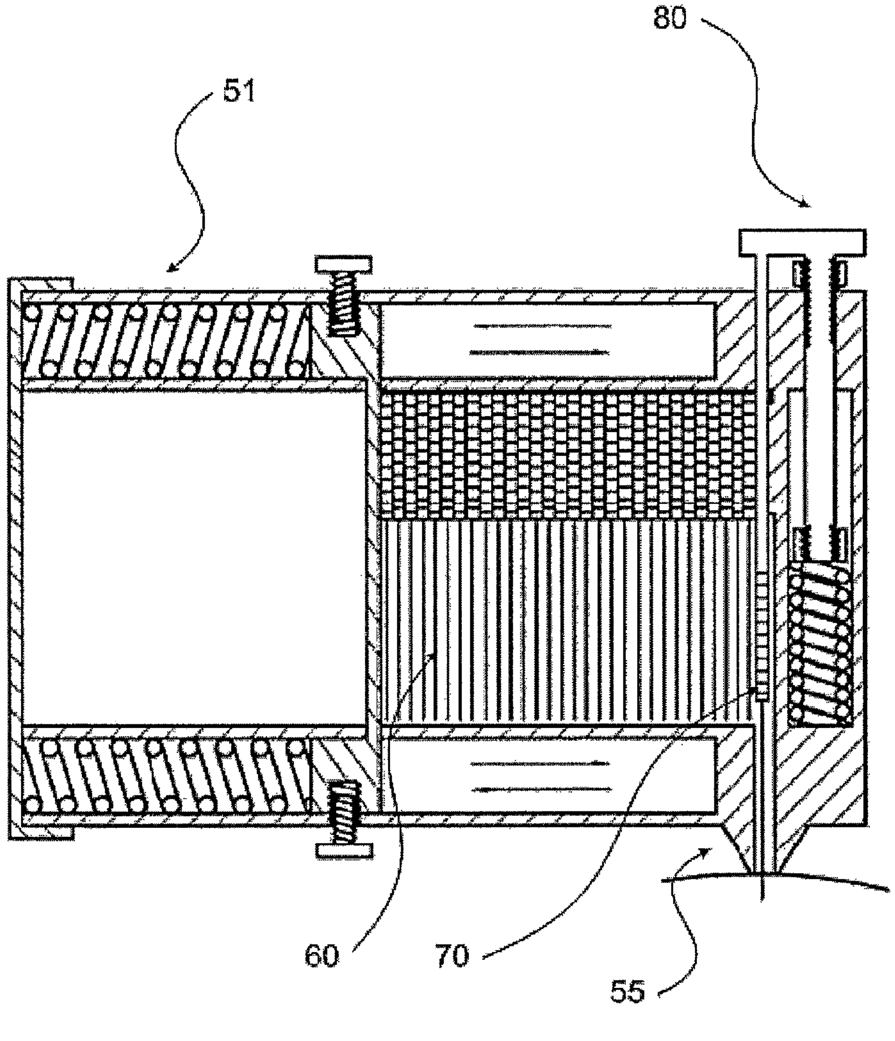

【Figure 2】
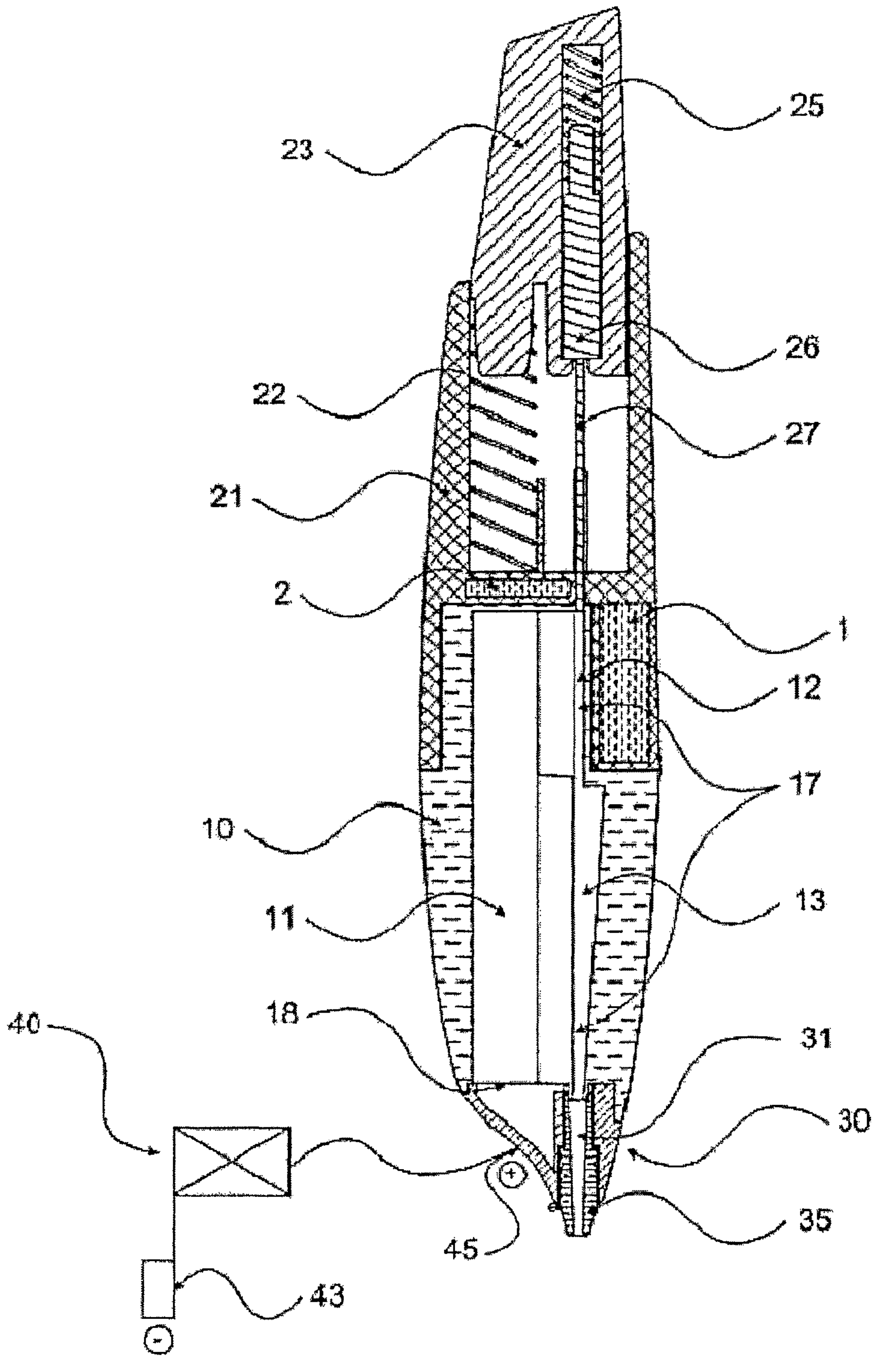

【Figure 3】
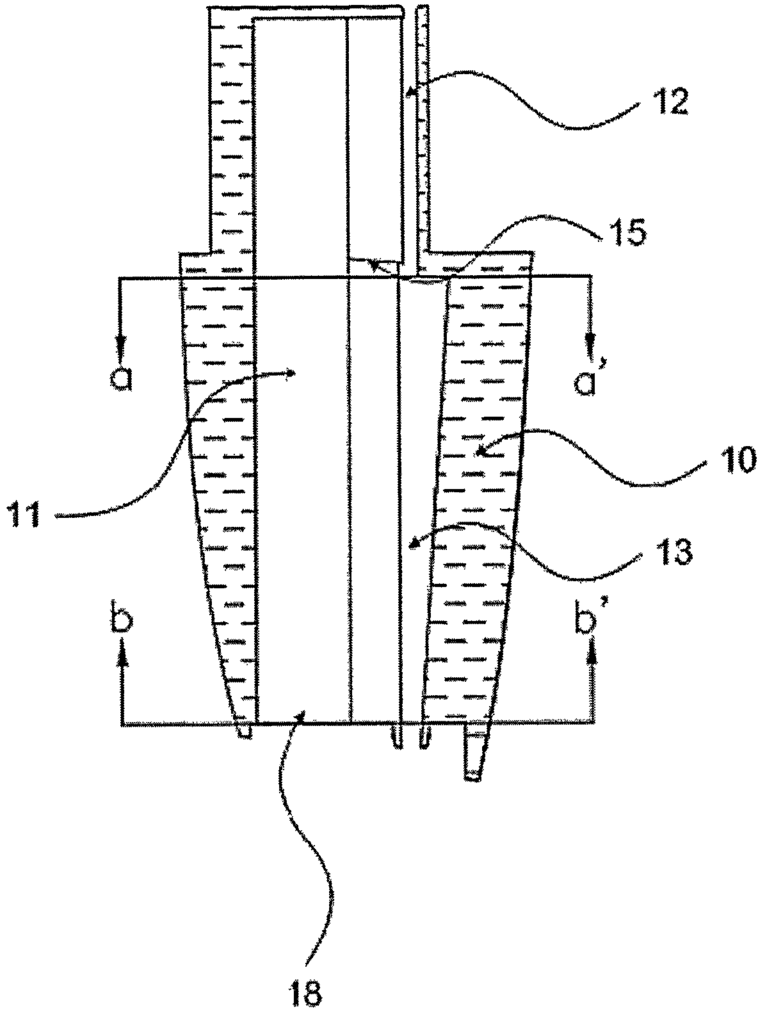
【Figure 4】
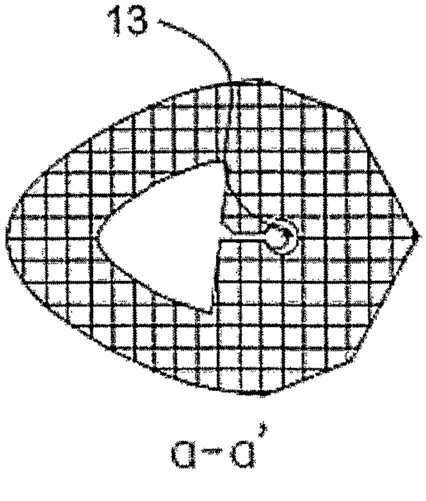

【Figure 5】
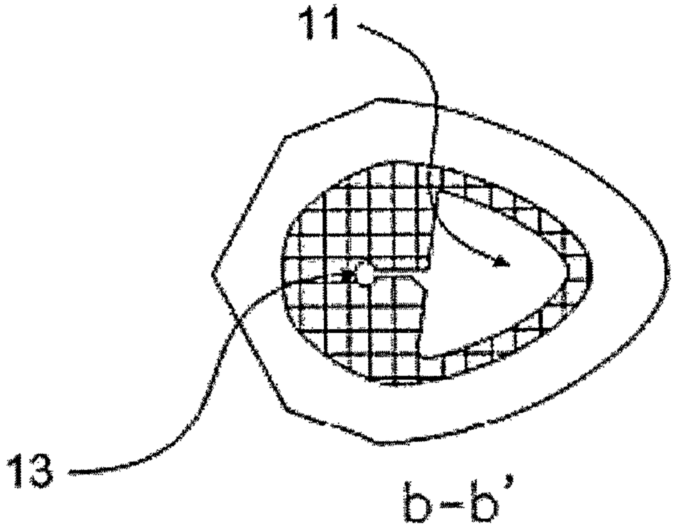
【Figure 6】
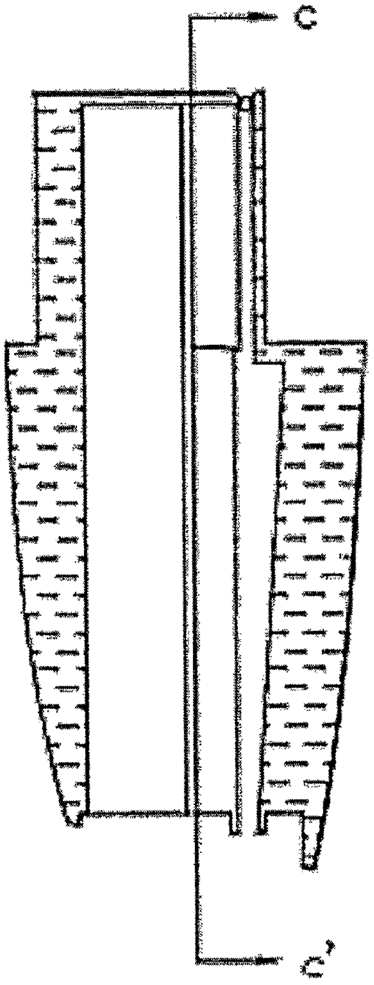

【Figure 7】
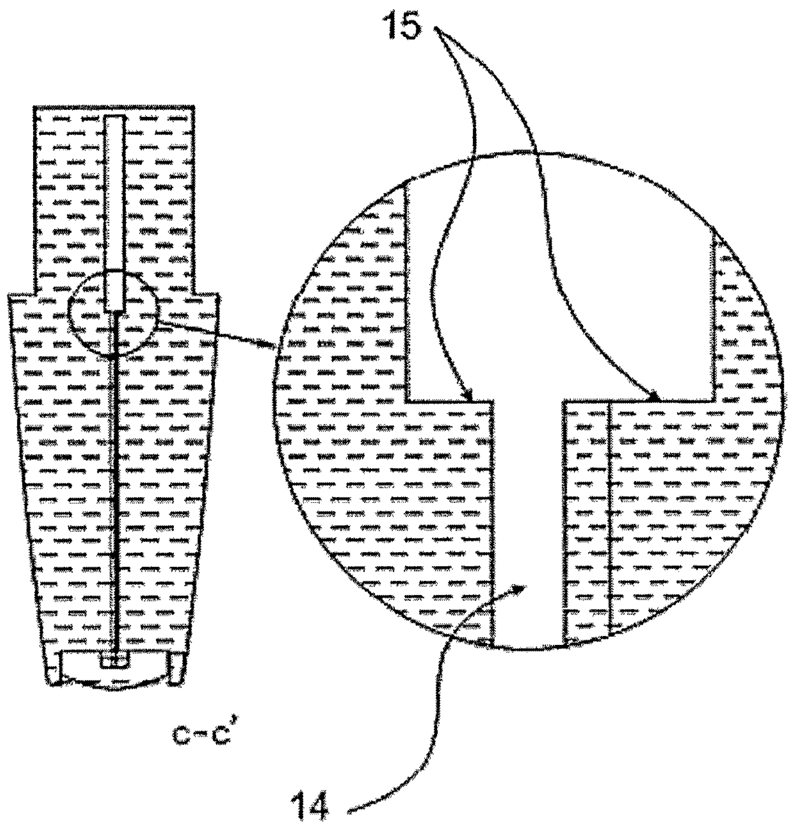
【Figure 8】
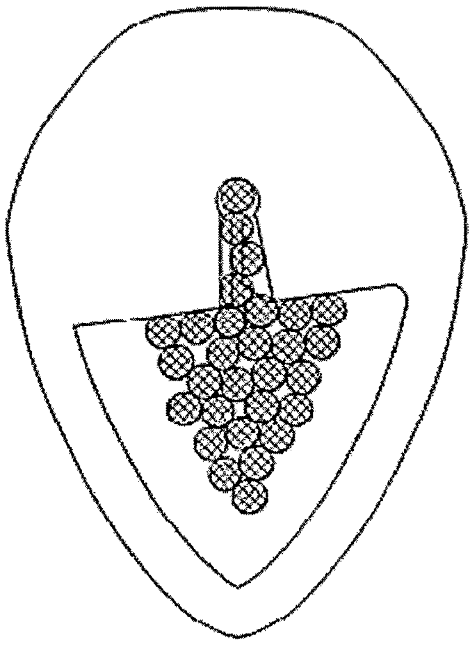

【Figure 9】
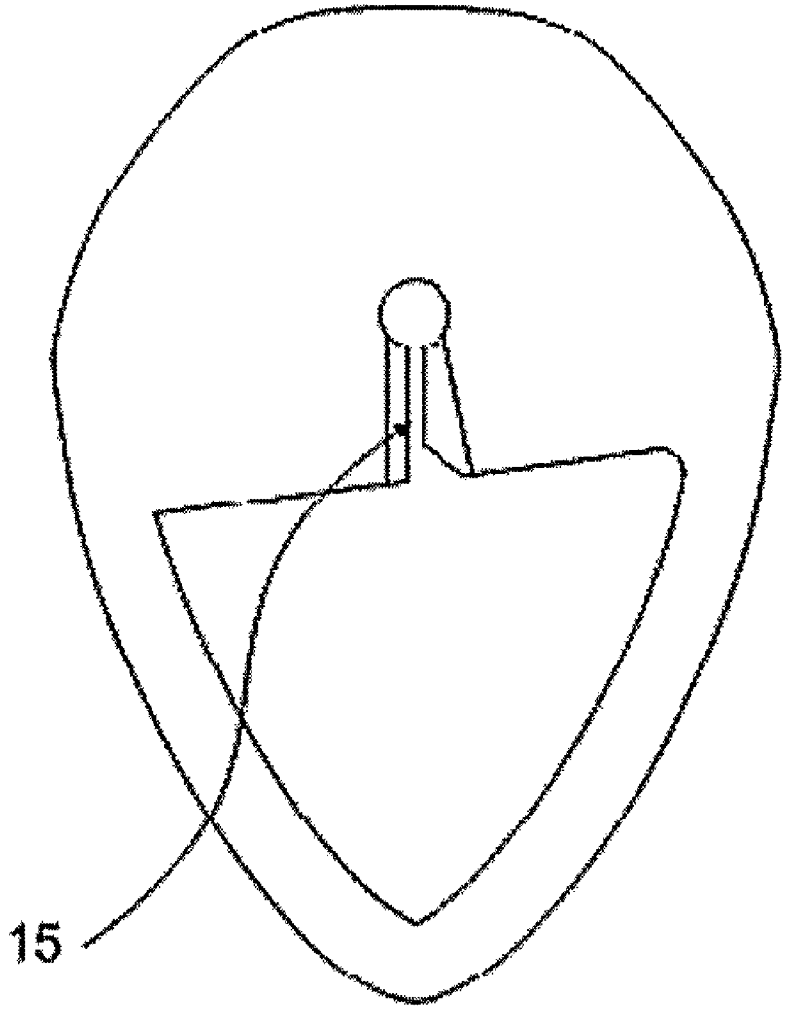

【Figure 10】
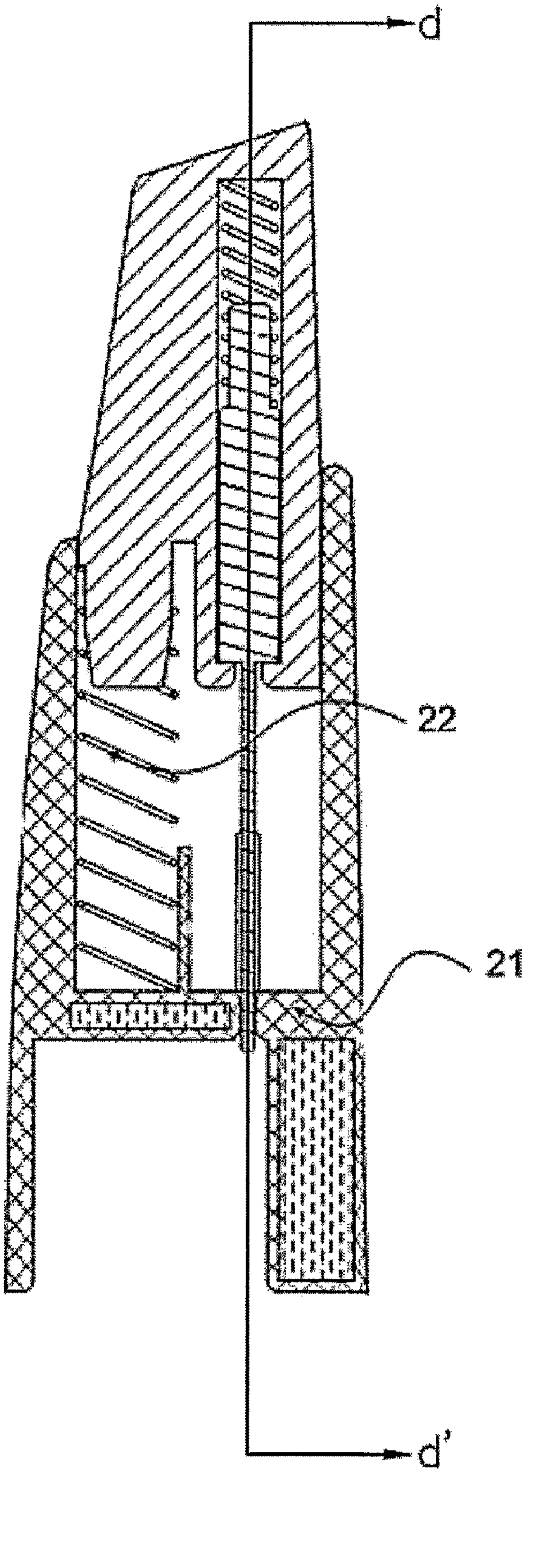

【Figure 11】
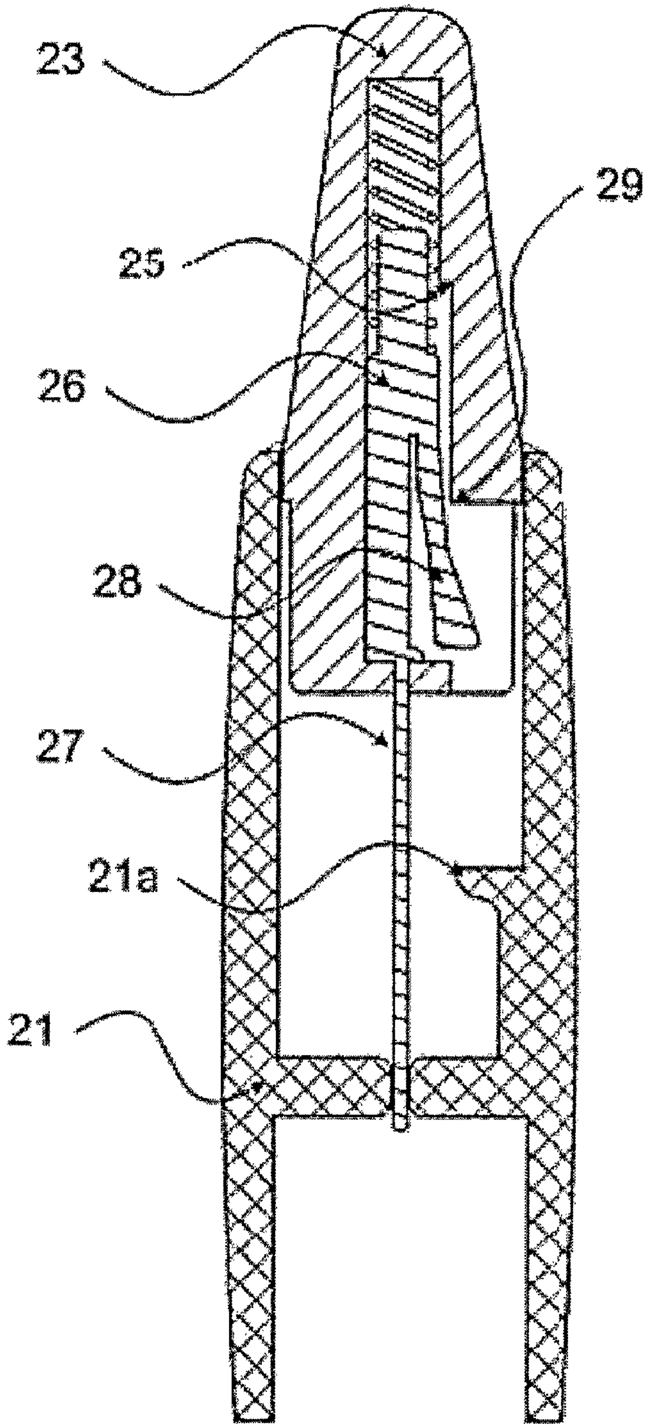
d-d'

【Figure 12】
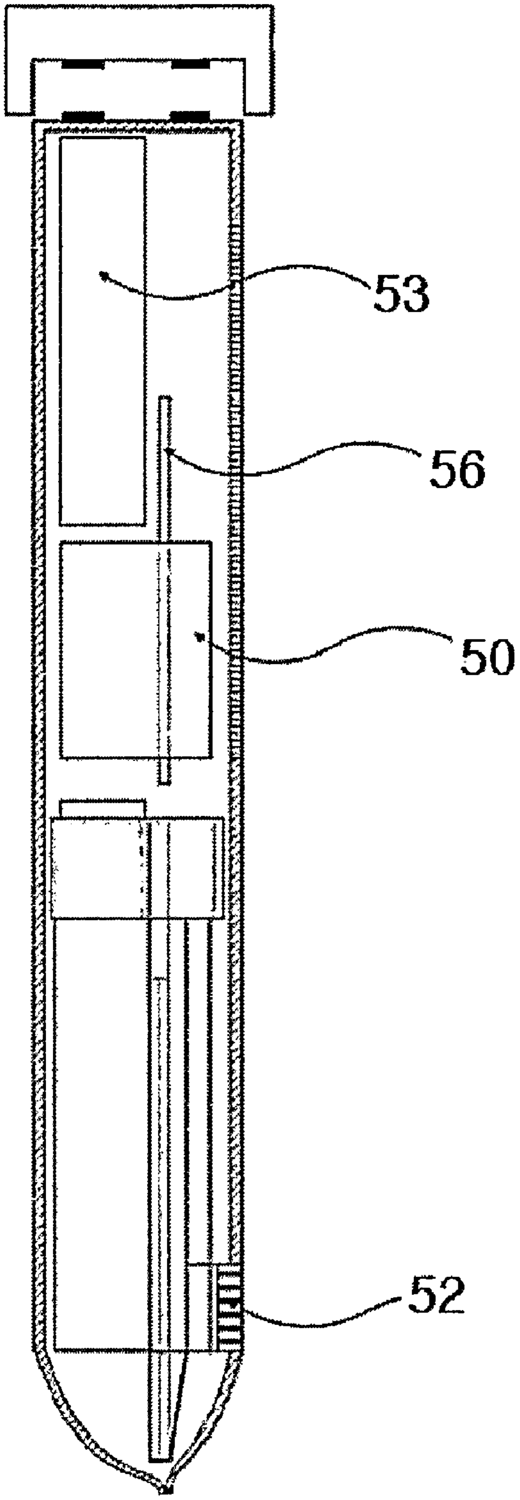

CONSECUTIVE ACUPUNCTURE DEVICE

TECHNICAL FIELD

The present invention relates to a pen-type consecutive acupuncture device which is convenient to grasp using one hand and conduct acupuncture, and more particularly to a consecutive acupuncture device which allows acupuncture to be consecutively conducted by pressing a button using one hand, with one or more needles in an envelope directly and randomly put into a needle storage cartridge and stored therein in a disarranged state, thereby shortening an acupuncture conduction time and permitting a user to conduct acupuncture in a convenient and hygienic manner, hides a needle from a patient, thereby freeing the patient from uneasiness of undergoing acupuncture, and adopts an instantaneous needle striking system, thereby significantly relieving the patient's pain when conducting acupuncture.

BACKGROUND ART

Up to now, a number of patent documents have disclosed various techniques related to acupuncture devices. For example, Korean Patent No. 10-497115 discloses a consecutive acupuncture device.

Referring to FIG. 1, such a consecutive acupuncture device comprises a needle storage section 60 for storing a plurality of needles 70 side by side, needle moving means 51 for pushing the stored needles 70 toward a needle projecting section 55, and an acupuncture conduction section 80 for pressing one needle 70 through the needle projecting section 55 to insert the needle 70 into a specified site of the body.

However, this kind of conventional consecutive acupuncture device has a problem in that, since the plurality of needles 70 are stored side by side, the device has a substantial size so that it is inconvenient for a user to conduct acupuncture by grasping the device using one hand.

Also, in the conventional consecutive acupuncture device, because the needles 70 must be stored one by one and side by side, a great deal of effort and time is required to store the needles 70.

Further, in the conventional consecutive acupuncture device, due to the fact that each needle 70 is gradually inserted into an afflicted part of the body, as in the case of using a conventional needle tube, an acupuncture conduction time is lengthened, so that a patient feels a pain.

DISCLOSURE OF INVENTION

Technical Problem

Accordingly, the present invention has been made keeping in mind the above problems occurring in the prior art, and an object of the present invention is to provide a pen-type consecutive acupuncture device which is convenient to grasp using one hand and conduct acupuncture, allows acupuncture to be consecutively conducted by pressing a button using one hand, with needles in an envelope randomly put into a cartridge and stored therein in a disarranged state, thereby providing user convenience and shortening an acupuncture conduction time.

Another object of the present invention is to provide a consecutive acupuncture device which hides a needle from a patient, thereby freeing the patient from uneasiness of undergoing acupuncture, and adopts an instantaneous needle striking system, thereby significantly relieving the patient's pain while conducting acupuncture.

Still another object of the present invention is to provide a consecutive acupuncture device which can conduct acupuncture at an exact acupuncture spot due to the presence of an acupuncture spot detection unit connected thereto.

Technical Solution

In order to achieve the above object, according to one aspect of the present invention, there is provided a consecutive acupuncture device for consecutively inserting needles into afflicted sites of the body, the device comprising a cartridge charged with and storing one or more needles; a first magnet positioned at a side of the cartridge to pull a needle stored in the cartridge by magnetic force and automatically place the needle at a striking position; striking means positioned on the cartridge to strike the needle placed at the striking position and insert the needle into an afflicted site of the body; and a discharge section positioned underneath the cartridge and defined with a hole through which the needle struck by the striking means is discharged.

According to another aspect of the present invention, the device further comprises a second magnet positioned on the cartridge, to suspend the needles stored in the cartridge and to prevent pointed ends of the needles from being brought into contact with a bottom surface of the cartridge.

According to another aspect of the present invention, the cartridge is defined with a slot which communicates with a needle storage space and allows the needles to pass through it only one by one, and a passage is defined in the cartridge to communicate with an end of the slot such that the needle struck by the striking means can be moved through the passage to then be discharged through the discharge section.

According to another aspect of the present invention, the device further comprises a guide coupled to the discharge section such that the guide can be extended out of and retracted into the discharge section to adjust a depth to which the needle is inserted into the body.

According to another aspect of the present invention, the device further comprises an acupuncture spot detection unit connected to the guide or the discharge section and having one terminal which is formed on the guide or the discharge section and the other terminal which is configured to be brought into contact with a portion of the body.

According to still another aspect of the present invention, the striking means comprises a button installed on the cartridge and biased upward by a first spring; a striking rod installed in the button and biased downward by a second spring; a nose part formed on a side of the striking rod and having an inclined surface; an engagement projection positioned below the nose part such that, when the button is pressed, the nose part is engaged with the engagement projection to compress the second spring to a predetermined degree; and a release protuberance brought into contact with the nose part such that, when the second spring is compressed to the predetermined degree, the release protuberance presses the inclined surface of the nose part to disengage the nose part from the engagement projection.

According to yet still another aspect of the present invention, the striking means comprises a switch manipulated by a user; an actuator driven by receiving power upon manipulation of the switch; and a striking rod raised and lowered by the actuator to strike the needle toward the afflicted site of the body.

BRIEF DESCRIPTION OF THE DRAWINGS

FIG. 1 is a sectional view of a conventional consecutive acupuncture device;

FIG. 2 is a longitudinal sectional view of a consecutive acupuncture device in accordance with the present invention;

FIG. 3 is a schematic view illustrating a needle insertion opening and a lower discharge hole of a cartridge which is a component element of the consecutive acupuncture device according to the present invention;

FIG. 4 is a sectional view taken along the line a-a' of FIG. 3;

FIG. 5 is a sectional view taken along the line b-b' of FIG. 3;

FIG. 6 is a schematic view illustrating a slot and shoulders of the cartridge which is a component element of the consecutive acupuncture device according to the present invention;

FIG. 7 is a partially-enlarged sectional view taken along the line c-c' of FIG. 6;

FIGS. 8 and 9 are schematic views illustrating the disarranged state of needles stored in the cartridge;

FIG. 10 is a schematic sectional view illustrating an instantaneous striking mechanism using a spring;

FIG. 11 is a sectional view taken along the line d-d' of FIG. 10; and

FIG. 12 is a schematic view illustrating an embodiment of an actuator-type consecutive acupuncture device.

BEST MODE FOR CARRYING OUT THE INVENTION

Reference will now be made in greater detail to a preferred embodiment of the invention, an example of which is illustrated in the accompanying drawings. Wherever possible, the same reference numerals will be used throughout the drawings and the description to refer to the same or like part.

A consecutive acupuncture device in accordance with an embodiment of the present invention will be described below with reference to FIGS. 2 through 12.

The consecutive acupuncture device has a characterizing feature in that, in consideration of user convenience and hygiene, when needles received in a sterilized envelope are directly and randomly put into a cartridge 10 to be maintained in a disarranged state, the needles are sequentially and automatically loaded to a striking position. The consecutive acupuncture device is most effective when it has a pen-shaped configuration.

To this end, the consecutive acupuncture device according to the present invention comprises a first magnet 1 and a second magnet 2 which are respectively located on a side and the top of the cartridge 10 to automatically load one by one the needles stored in a disarranged state to the striking position, striking means which is positioned on the cartridge 10 to strike the loaded needle, and a discharge section 30 which is positioned on the bottom of the cartridge 10 to discharge the struck needle.

Referring to FIGS. 2 through 7, the cartridge 10 defines a needle storage space 11.

A slot 14 is defined in the cartridge 10 to communicate with the needle storage space 11 such that the needles are sequentially attracted one by one into the slot 14 by magnetic force of the first magnet 1. A discharge hole 17 is also defined in the cartridge 10 to communicate with the end of the slot 14 such that struck needle can be reliably discharged through the discharge hole 17 and inserted into an afflicted site of the human body.

As a consequence, the cartridge 10 is configured such that sterilized needles can be directly and randomly put from an envelope into the needle storage space 11 in a state in which even the heads of the needles are not touched.

The slot 14 is defined to have a size slightly greater than that of the needles, and shoulders 15 are formed in the middle of the slot 14 so that the lower end of the head of each needle is captured between the shoulders 15 and thereby an adjoining needle is prevented from being unintentionally discharged by frictional force applied from a struck needle when the struck needle is discharged through the discharge hole 17.

Preferably, the discharge hole 17 through which the struck needle is discharged is defined such that the lower part 13 of the discharge hole 17 which is positioned below the shoulders 15 has a size greater than that of the upper part 12 of the discharge hole 17 which is positioned above the shoulders 15, to avoid interference with an adjoining needle. It is preferred that the lower part 13 of the discharge hole 17 have a funnel-shaped cross-section to have a minimum size to thereby avoid interference with an adjoining needle upon discharge of a struck needle.

When assembling the consecutive acupuncture device, the first magnet 1 is installed in a housing 21 of the striking means to be positioned outward of the slot 14 of the cartridge 10. The first magnet 1 functions to attract each needle by magnetic force and automatically load the attracted needle to the striking position in the cartridge 10.

When assembling the consecutive acupuncture device, the second magnet 2 is installed in the housing 21 of the striking means to be positioned on the top of the cartridge 10. The second magnet 2 functions to suspend each needle by magnetic force and prevent the pointed end of each needle from being brought into contact with the bottom of the cartridge 10 and from being damaged thereby.

The striking means is placed on the cartridge 10 and functions to strike a needle which is held in the striking position and insert the needle into an afflicted site of the human body. The spring-type striking means as shown in FIGS. 10 and 11 comprises the housing 21 assembled to the upper part of the cartridge 10, a button 23 installed in the housing 21 and biased upward by a first spring 22, and a striking rod 26 installed in the button 23 and biased downward by a second spring 25. An operating arm 27 is integrally formed on the lower end of the striking rod 26 and extends downwards toward the needle held in the striking position. The striking rod 26 has a nose part 28 which is formed on a side of the striking rod 26 and possesses an inclined surface of an upward slope. In correspondence to the nose part 28 of the striking rod 26, an engagement projection 21*a* is formed on the inner surface of the housing 21 such that, when the button 23 is pressed, the nose part 28 is engaged with the engagement projection 21*a* to compress the second spring 25 to a predetermined degree. A release protuberance 29 is formed on the inner surface of the button 23 above the nose part 28 such that, when the second spring 25 is compressed to the predetermined degree, the release protuberance 29 presses the inclined surface of the nose part 28 to disengage the nose part 28 from the engagement projection 21*a*.

In the actuator-type striking means as shown in FIG. 12, a striking rod 56 is lowered upon actuation of a driver 50 to strike a needle. As the driver 50, various driving means, such as a solenoid or a motor constructed to operate by receiving power from a battery 53 upon manipulation of a switch 52, can be used.

The discharge section 30 is installed to be positioned under the cartridge 10. A hole 31, through which a struck needle is discharged, is defined through the discharge section 30 to extend vertically. A guide 35 for adjusting the depth by which the struck needle is inserted into the skin is installed in the hole 31. The guide 35 is threadedly coupled in the hole 31 of the discharge section 30 to be adjusted in the length through which the guide 35 projects beyond the lower end of the discharge section 30 and thereby adjust the depth by which the struck needle is inserted into the skin.

An acupuncture spot detection unit 40 functions to measure the impedance of the human body and detect an acupuncture spot corresponding to an afflicted site of the human body. The acupuncture spot detection unit 40 has one terminal 43 which is brought into contact with a portion of the human body and the other terminal 45 which is formed on the guide 35 made of a conductive material. Therefore, by moving the guide 35 on the afflicted site of the human body, the acupuncture spot can be easily detected.

Hereafter, an operation mechanism of the consecutive acupuncture device according to the present invention constructed as mentioned above will be described.

The consecutive acupuncture device is prepared by opening an envelope in which sterilized needles are received, randomly putting the needles into the cartridge 10, coupling the discharge section 30 to an introduction opening 18 to close the introduction opening 18, and assembling the striking means to the upper part of the cartridge 10.

In this state, by bringing the discharge section 30 into contact with the afflicted site of the human body and pressing the button 23 by no less than a predetermined length as shown in FIG. 11, the nose part 28 of the striking rod 26 installed in the button 23 is engaged with the engagement projection 21*a*, and the second spring 25 for elastically supporting the striking rod 26 is compressed. By further pressing the button 23 downwards by no less than a pre-selected length, the release protuberance 29 presses the inclined surface of the nose part 28, and the nose part 28 is disengaged from the engagement projection 21*a*. Thereupon, the striking rod 26 is shot by the elastic force of the second spring 25, and the needle held in the striking position is instantaneously struck by the striking rod 26. In this way, since the needle is instantaneously struck by the striking rod 26, it is possible to minimize the pain caused when undergoing acupuncture. When compared to the conventional method, in which a needle tube is used to insert each needle into an afflicted site of the human body, because the striking speed is significantly increased, pain can be markedly relieved.

Also, while the needle struck by the striking rod 26 tends to pull an adjoining needle toward the discharge section 30 due to the frictional force applied by the head of the struck needle, since the head of the adjoining needle is captured between the shoulders 15 formed in the middle of the slot 14, the adjoining needle is prevented from being unintentionally discharged.

After striking the needle, by raising the consecutive acupuncture device from the afflicted site of the human body, the needle is completely discharged out of the consecutive acupuncture device and remains inserted in the skin. At this time, due to the fact that the lower part 13 of the discharge hole 17 has a size greater than that of the upper part 12 of the discharge hole 17, it is possible to avoid interference with an adjoining needle, as a result of which the inserted needle can remain as it is when the device is raised.

Next, by releasing the pressed button 23, the striking rod 26 is returned to its original position by the first spring 22, and another needle in a standby state is automatically attracted and loaded to the striking position by the magnetic force of the first magnet 1.

By repeating the above-described procedure, one or more needles can be consecutively inserted into the afflicted sites in a human body.

INDUSTRIAL APPLICABILITY

As is apparent from the above descriptions, the consecutive acupuncture device according to the present invention provides advantages in that one or more needles can be quickly charged into a cartridge in a convenient and hygienic manner and a user can conduct acupuncture within a short period of time by consecutively using a plurality of needles.

Further, because a needle is not viewed by a patient, the patient can be freed from uneasiness of undergoing acupuncture. Also, due to the fact that an instantaneous needle striking system is adopted, the patient's pain can be significantly relieved while undergoing acupuncture.

Although a preferred embodiment of the present invention has been described for illustrative purposes, those skilled in the art will appreciate that various modifications, additions and substitutions are possible, without departing from the scope and spirit of the invention as disclosed in the accompanying claim.

The invention claimed is:

1. A consecutive acupuncture device for consecutively inserting needles into afflicted sites of the body, the device comprising:

- a cartridge charged with and storing one or more needles;
- a first magnet positioned at a side of the cartridge to pull a needle stored in the cartridge by magnetic force and automatically place the needle at a striking position;
- a striking element positioned on the cartridge to strike the needle placed at the striking position and insert the needle into an afflicted site of the body;
- a discharge section positioned underneath the cartridge and defined with a hole through which the needle struck by the striking element is discharged; and
- a second magnet positioned on top of the cartridge above and adjacent to the head ends of the needles, the second magnet facing the head ends of the needles and being configured to suspend the needles stored in the cartridge and to prevent pointed ends of the needles from being brought into contact with a bottom surface of the cartridge.

2. The device as set forth in claim 1, wherein the cartridge is defined with a slot which communicates with a needle storage space and allows the needles to pass through it only one by one, and a passage is defined in the cartridge to communicate with an end of the slot such that the needle struck by the striking element can be moved through the passage to then be discharged through the discharge section.

3. The device as set forth in claim 1, further comprising: a guide coupled to the discharge section such that the guide can be extended out of and retracted into the discharge section to adjust a depth to which the needle is inserted into the body.

4. The device as set forth in claim 1 or 3, further comprising: an acupuncture spot detection unit having one terminal which is formed on the discharge section and the other terminal which is configured to be brought into contact with a portion of the body.

5. The device as set forth in claim 1, wherein the striking element comprises:

- a button installed on the cartridge and biased upward by a first spring;
- a striking rod installed in the button and biased downward by a second spring;
- a nose part formed on a side of the striking rod and having an inclined surface;
- an engagement projection positioned below the nose part such that, when the button is pressed, the nose part is engaged with the engagement projection to compress the second spring to a predetermined degree; and
- a release protuberance brought into contact with the nose part such that, when the second spring is compressed to the predetermined degree, the release protuberance presses the inclined surface of the nose part to dispense the nose part from the engagement projection.

6. The device set forth in claim 1, wherein the striking element comprises:

a switch manipulated by a user;

an actuator driven by receiving poser upon manipulation of the switch; and a striking rod raised and lowered by the actuator to strike the needle toward the afflicted site of the body.

* * * * *